US012636174B2

(12) United States Patent
Stappenbeck et al.

(10) Patent No.: US 12,636,174 B2
(45) Date of Patent: May 26, 2026

(54) LOADING DEVICE AND METHOD FOR LOADING A PROSTHESIS

(71) Applicant: TRICARES SAS, Paris (FR)

(72) Inventors: Nadine Stappenbeck, Munich (DE); Helmut Straubinger, Aschheim (DE); Georg Rahmig, Pforzheim (DE)

(73) Assignee: TRICARES SAS, Paris (FR)

( * ) Notice: Subject to any disclaimer, the term of this patent is extended or adjusted under 35 U.S.C. 154(b) by 728 days.

(21) Appl. No.: 17/312,192

(22) PCT Filed: Dec. 17, 2019

(86) PCT No.: PCT/EP2019/085688
§ 371 (c)(1),
(2) Date: Jun. 9, 2021

(87) PCT Pub. No.: WO2020/127293
PCT Pub. Date: Jun. 25, 2020

(65) Prior Publication Data
US 2022/0054289 A1 Feb. 24, 2022

(30) Foreign Application Priority Data
Dec. 20, 2018 (EP) .................................... 18214986

(51) Int. Cl.
*A61F 2/95* (2013.01)
*A61F 2/24* (2006.01)
(52) U.S. Cl.
CPC .......... *A61F 2/9525* (2020.05); *A61F 2/2427* (2013.01); *A61F 2220/0025* (2013.01); *A61F 2250/0039* (2013.01)

(58) Field of Classification Search
CPC .................. A61F 2/9525; A61F 2/2427; A61F 2220/0025; A61F 2250/0039; A61F 2/9522; A61F 2/2412
See application file for complete search history.

(56) References Cited

U.S. PATENT DOCUMENTS

| | | | |
|---|---|---|---|
| 5,749,921 A | 5/1998 | Lenker et al. | |
| 5,840,081 A | 11/1998 | Andersen et al. | |
| 8,070,800 B2 | 12/2011 | Lock et al. | |
| 9,782,256 B2 | 10/2017 | Zeng | |
| 10,039,639 B2 | 8/2018 | Marchand et al. | |
| 10,952,851 B2 | 3/2021 | Marchand | |
| 2004/0049207 A1 | 3/2004 | Goldfarb et al. | |
| 2004/0186563 A1 | 9/2004 | Lobbi | |

(Continued)

FOREIGN PATENT DOCUMENTS

| | | |
|---|---|---|
| EP | 3071151 B2 | 7/2017 |
| EP | 3752098 A1 | 12/2020 |

(Continued)

OTHER PUBLICATIONS

Written Opinion of the International Searching Authority for International Application No. PCT/EP2019/085688 (Year: 2020).*

(Continued)

*Primary Examiner* — Christopher J. Besler
(74) *Attorney, Agent, or Firm* — The Dobrusin Law Firm, P.C.

(57) ABSTRACT

The present invention relates to a heart valve prosthesis loading device and a method for loading a heart valve prosthesis onto a delivery system.

17 Claims, 11 Drawing Sheets

(56)                    References Cited

U.S. PATENT DOCUMENTS

| | | | |
|---|---|---|---|
| 2005/0137697 | A1 | 6/2005 | Salahieh |
| 2006/0020327 | A1 | 1/2006 | Lashinski |
| 2007/0005129 | A1 | 1/2007 | Damm et al. |
| 2007/0244552 | A1 | 10/2007 | Salahieh |
| 2007/0270679 | A1 | 11/2007 | Nguyen et al. |
| 2008/0086107 | A1 | 4/2008 | Roschak |
| 2009/0005863 | A1 | 1/2009 | Goetz |
| 2009/0054976 | A1 | 2/2009 | Tuval et al. |
| 2010/0022948 | A1 | 1/2010 | Wilson et al. |
| 2010/0256754 | A1 | 10/2010 | Styre |
| 2010/0292779 | A1 | 11/2010 | Straubinger et al. |
| 2010/0292780 | A1* | 11/2010 | Straubinger ............. A61F 2/95 |
| | | | 623/1.23 |
| 2011/0029072 | A1 | 2/2011 | Gabbay |
| 2011/0046712 | A1 | 2/2011 | Melsheimer et al. |
| 2011/0160836 | A1 | 6/2011 | Behen |
| 2012/0083874 | A1 | 4/2012 | Dale et al. |
| 2012/0209122 | A1 | 8/2012 | Garbini et al. |
| 2013/0204357 | A1 | 8/2013 | Thill et al. |
| 2013/0274855 | A1 | 10/2013 | Stante et al. |
| 2013/0304200 | A1 | 11/2013 | McLean et al. |
| 2014/0144000 | A1 | 5/2014 | Creaven et al. |
| 2014/0303719 | A1 | 10/2014 | Cox |
| 2014/0331475 | A1 | 11/2014 | Duffy et al. |
| 2017/0290661 | A1 | 10/2017 | Von Segesser |
| 2018/0092744 | A1* | 4/2018 | von Oepen ........... A61F 2/2439 |
| 2018/0325667 | A1 | 11/2018 | Gallagher et al. |
| 2020/0008941 | A1 | 1/2020 | Stappenceck et al. |
| 2020/0360141 | A1 | 11/2020 | Stappenceck et al. |

FOREIGN PATENT DOCUMENTS

| | | | |
|---|---|---|---|
| WO | 2001/064137 | A1 | 9/2001 |
| WO | 2006/128185 | A2 | 11/2006 |
| WO | 2008/118481 | A1 | 10/2008 |
| WO | 2009/106545 | A1 | 9/2009 |
| WO | 2009/137712 | A1 | 11/2009 |
| WO | 2012/178115 | A2 | 12/2012 |
| WO | 2013/104721 | A1 | 7/2013 |
| WO | 2015/107226 | A1 | 7/2015 |
| WO | 2016/090025 | A1 | 6/2016 |
| WO | 2017/195125 | A1 | 11/2017 |
| WO | 2020/127372 | A1 | 6/2020 |

OTHER PUBLICATIONS

International Search Report and Written Opinion, Application No. PCT/EP2019/085688 dated Feb. 10, 2020.

* cited by examiner 101    102    103    104    105    106    107    108

103    104  101  105    106    102    107    108

103   104   101   105   106   107   108   102

110

111

113

112

110

111

113

112

LOADING DEVICE AND METHOD FOR LOADING A PROSTHESIS

CLAIM OF PRIORITY

This application is a national phase filing under 35 USC § 371 from PCT Patent Application serial number PCT/EP2019/085688 filed on Dec. 17, 2019, and published as WO 2020/0127293 A1 on Jun. 25, 2020, which claims priority to European Patent Application Number EP 18214986.4 filed on Dec. 20, 2018. PCT Patent Application serial number PCT/EP2019/085688 and European Patent Application Number EP 18214986.4 are each incorporated by reference herein in its entirety.

FIELD

The present invention relates to a heart valve prosthesis loading device and a method for loading a replacement heart valve prosthesis onto a delivery system.

BACKGROUND

In the last decades minimal invasive techniques have advanced and are now possible in many medical fields.

In recent years the treatment of heart valve diseases and defects has become more and more successful. Examples are transapical, transjugular and transfemoral procedures for heart valve replacement therapies, e.g., aortic and mitral heart valve treatments.

In many cases a stent-based prosthesis with a tissue-based replacement valve, e.g. pericardium, is used and implanted to replace the endogenous heart valve by way of a catheter or delivery system.

The prosthesis has to be crimped and loaded onto the delivery system and a number of systems have been described in the art.

Known crimping devices work e.g., as follows: the transcatheter heart valve prostheses are crimped using a radial crimper or a set of funnels, through which the prostheses are pushed. Radial crimpers are utilized for stainless steel stents as they maintain their crimped state once the force of the radial crimper is released. Self-expanding nitinol stents usually get pushed through one or several funnels, which reduces their diameter. However, these stents are commonly laser cut stents. The rigid structure of a laser cut stent can transfer force in a longitudinal direction, without compressing. This is a prerequisite to allow for pushing a stent through a funnel.

When crimping a self-expandable prosthesis, the stent/implant is commonly pushed through a funnel, which decreases its diameter gradually down to the inner diameter of the delivery system. At that stage the crimped end of the device is engaged with the delivery system, usually by means of eyelets or similar features. A second funnel may then be utilized to crimp the opposite side of the implant so that the outer shaft of the delivery system can be advanced. A loading tube may be utilized in an intermediate step if required. Such devices and techniques may imply a number of disadvantages depending on the stent or prosthesis characteristics. In particular stents or prostheses exhibiting either different material characteristics or exhibiting low stiffness are difficult to be correctly crimped onto a delivery system. Moreover, crimping with inappropriate means and methods may imply damages to the stent or/and prosthesis tissue.

In order to be able to apply the above-described state of the art technique, it is required that the height and the diameter of the implant have a sufficiently high ratio, which ensures proper pushability when advancing the implant through the funnel. The design of the device and its material properties also determine its pushability. The stent/implant must be designed in a way that a push force applied to one side is evenly transferred to the opposite end of the device. If the stent/implant exhibits an insufficient pushability the technique described above cannot be applied.

Braided structures included in stents or prostheses imply challenges that cannot be overcome by current crimping tools. A heart valve prosthesis containing a braided Nitinol stent—due to its self-expansion property—cannot be crimped without disadvantages by way of a radial crimper because the stent would expand again as soon as the force of the radial crimper is released. The prosthesis would have to be maintained in a crimped state in order to be able to advance a delivery system shaft over it. When applying a longitudinal force to a braided stent, as would be the case when pushing it through a funnel, the stent would get compressed longitudinally, rather than advanced through the funnel. This could induce damage to the braided structure. Compressing the prosthesis within the funnel would also not allow for proper crimping.

One problem in current crimping and loading tools is that forces are applied to the stent in order to crimp and load it onto a delivery system. This in turn can lead to damaging the tissue of the replacement valve with detrimental consequences for the functioning of the prosthesis in situ after deployment. Another problem is to achieve a symmetrical crimping and loading of the prosthesis which is difficult in view of the forces applied during the crimping procedure. Yet another problem is to achieve a small diameter in the crimped state without damaging not only the tissue valve but neither damage the stent component by way of non-symmetrical crimping or by way of non-symmetrical forces applied onto the stent component. Yet another problem arises if different stent materials or materials with different material characteristics due to different diameters or thickness dimensions or due to different structures or different foreshortening are used.

One example of a braided stent-based prosthesis is disclosed in WO2015/107226A1 including a Nitinol inner stent cut of a Nitinol tube and an outer stent of a braided Nitinol material wherein the pericardial replacement valve is attached to the inner stent. Such a stent-based prosthesis is difficult to crimp and load onto a catheter due to its different material structures and characteristics.

Laser cut stents made of one part or composed of two or more stent parts need also be loaded onto a delivery system in a manner that provides for a correct, symmetrical and reproducible loading onto the delivery system as well as does not impact the stent and prosthesis overall which may jeopardize the correct functioning of the prosthesis after implantation. More so, one has to make sure that the loading procedure does not introduce micro damages to the prosthesis which may shorten long term functioning of the prosthesis. In laser cut stents which exhibit a low stiffness a loading procedure and loading devices based upon the concept of pushing the stent through the loading device imply problems and may not meet all the criteria as pointed out above for a smooth and correct loading of the prosthesis on the delivery system.

A problem in tricuspid replacement heart valve prostheses is also that due to the geometry of the native tricuspid valve also the replacement heart valve has to exhibit a relative large diameter and a relative short length/height. During the loading and crimping procedure this ratio is inverted and thus the crimped prosthesis is extended in length. This is in contrast to other replacement heart valves, e.g. an aortic replacement heart valve, wherein the ratio remains essentially the same. This inversion of the diameter:length ratio implies problems for a correct loading and in particular the risk of damage to the prosthesis during crimping and loading.

Accordingly, it is one object to provide a crimping and loading device or assembly of parts reducing the disadvantages of the prior art or essentially avoiding these disadvantages.

It is another object to provide a crimping and loading device or assembly of parts useful for crimping and/or loading on a catheter a stent-based prosthesis which comprises low stiffness and/or at least two different stent material characteristics or/and two different stent materials, and which reduces the disadvantages of the prior art or essentially avoids these disadvantages.

It is another object to provide a method for crimping and/or loading a stent-based prosthesis which comprises low stiffness and/or at least two different stent material characteristics and/or two different stent materials, and which reduces the disadvantages of the prior art or essentially avoids these disadvantages.

It is another object to provide a method for crimping and/or loading a stent-based prosthesis which comprises a low stiffness and/or a braided stent component, and which reduces the disadvantages of the prior art or essentially avoids these disadvantages.

BRIEF SUMMARY OF THE DISCLOSURE

In one aspect the disclosure relates to pulling means useful for loading a stent or prosthesis onto a delivery system wherein the pulling means has a first diameter, a second diameter and at least three connecting means, preferably mechanical, for linkage with a stent or prosthesis.

In one aspect the disclosure relates to a loading device useful for loading a stent or prosthesis onto a delivery system comprising a pulling means according to claims 1 to 5, a tapered part, e.g., a funnel, and a loading tube.

In another aspect the disclosure relates to a system comprising a pulling means according to any of claims 1 to 5 and a stent or prosthesis wherein the pulling means and the stent or prosthesis are mechanically connected and wherein said mechanically connected parts are releasably connected.

In another aspect the disclosure relates to a method for loading a stent or prosthesis onto a delivery system comprising the steps of i. connecting the stent or prosthesis with the pulling means, ii. pulling the stent or prosthesis into and through the tapered part, iii. followed by pulling the stent or prosthesis into the loading tube, iv. engaging the stent or prosthesis with the delivery system, and v. advancing an outer catheter shaft of the delivery system over the stent or prosthesis.

In another aspect the disclosure relates to a system comprising a delivery system, a pulling means or/and loading device and a medical device, e.g., a stent, a prosthesis or/and a replacement heart valve prosthesis.

BRIEF DESCRIPTION OF THE DRAWINGS

The invention is exemplified by the Figures which are not meant to be restrictive but only as exemplifying various possible embodiments according to the disclosure wherein.

DETAILED DESCRIPTION

Figure 1:
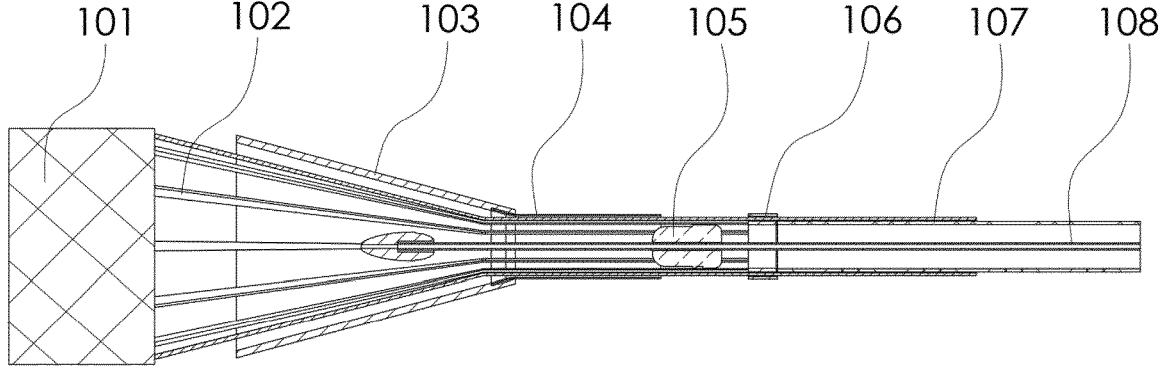
FIG. 1 illustrates a setup for loading a stent or prosthesis comprising pulling means according to the disclosure.

In the following certain terms of the disclosure will be defined. Otherwise, technical terms in the context of the disclosure shall be understood as by the applicable skilled person.

A "stent" or "prosthesis" in the sense of the disclosure is to be understood as a mesh, laser cut nitinol stent, made of plastic or a composite material. An example of a stent is disclosed in WO 2015/107226A1 or in EP 18 000 144.8 which disclosure is incorporated herein by reference. Stents and replacement heart valve prostheses useful according to the present disclosure are further illustrated in the Figures and the Figure description. A prosthesis in the sense of the disclosure is composed of or comprises a stent which is characterized by a low stiffness or which is essentially not push resistant.

In the sense of the disclosure being "not push resistant" or having "reduced push resistance" is to be understood in the sense that a stent or prosthesis will significantly deform when pushed into or against a resistance like e.g., a funnel or essentially cannot be pushed through e.g., a funnel without being essentially deformed or which cannot at all be pushed therethrough.

The term "assembly of parts", "crimping device" or "system" in the sense of the disclosure is to be understood as the parts used to compose the disclosed device and which parts are useful for either crimping the prosthesis or/and loading the prosthesis onto a catheter.

The term "catheter" or "delivery device" or "delivery system" in the sense of the disclosure is to be understood as a device used to deploy a prosthesis in a patient at a determined site, e.g., to replace a heart valve like an aortic replacement heart valve, a mitral replacement heart valve or a tricuspid replacement heart valve, or a stent.

The term "funnel" in the sense of the disclosure is to be understood as any part useful to reduce the diameter of a stent or stent-based prosthesis and which has a conical or tapered area or is essentially a conical or tapered part. This part may have varying sizes and may be made out of different materials or comprise different materials as appropriate for its use. It may comprise low friction materials like polytetrafluorethylene (Teflon®), polyoxymethylene (POM).

The term "pulling means" in the sense of the disclosure is to be understood as any means or part useful to exhibit a pulling force to a stent, a prosthesis, a wire, or a stretch of material. A pulling means in this sense may exhibit two ends or two areas or two portions with different diameters wherein the wider diameter may be reduced to the smaller diameter of the pulling means. It may be made of different materials as metal, nitinol, plastic or any useful material or a combination of different materials capable of exhibiting enough stability to perform a crimping or/and loading procedure for a stent or prosthesis. The wider diameter may be essentially the same diameter as the diameter of the prosthesis or stent in its expanded form or/and the smaller diameter may resemble the diameter of the prosthesis or stent when essentially fully crimped. The wider diameter can have from 60 to 80 mm and the smaller diameter can have from 7 to 10 mm.

A "pulling means guide" in the sense of the disclosure is to be understood as any means or part useful to reduce the wider diameter of the pulling means to the smaller diameter and that maintains the flexible arms of the pulling means at a defined equal distance to one another, preferably made of a stainless steel, nitinol, a composite material, a plastic or other useful material.

"Eyelet" in the sense of the disclosure is to be understood as a part at an end or within a stent or prosthesis (110) which can be connected with another part of an assembly of parts, e.g., a pulling means, by way of a counter part, e.g. a pocket (109), and with the stent holder of the delivery system.

"Connecting means" in the sense of the disclosure is a part on the pulling means that is useful for connecting the pulling means with the stent or prosthesis; it can have the form of a pocket.

"Pocket" in the sense of the disclosure is to be understood as a counterpart of an eyelet and which is useful for a releasable connection of two parts, e.g., an eyelet of a stent or prosthesis and a pocket on a pulling means or vice versa. It can also be denoted as connecting means.

A "mechanical link" in the sense of the disclosure is to be understood as a connection of two parts which can be connected and disconnected and are thus releasable connected.

The term "releasable" in the sense of the disclosure is to be understood as the connection of two parts, e.g., base parts or sutures or sutures and stent or a prosthesis or areas of a prosthesis, which connection may be de-connected at a pre-determined point in time or during the method described herein. The connection may be designed in a way that it is accessible with an appropriate tool or is designed in a manner so that the connection may be opened to de-connect the two respective parts.

The term "crimping" in the sense of the disclosure is to be understood as reducing the diameter of a prosthesis or stent from an expanded larger or wider diameter to a compressed or smaller diameter. The outer diameter of a crimped stent or prosthesis according to the disclosure may be 15 to 28 or 24 to 26 or 16 to 19 or 15 to 18 French.

The term "loading" in the sense of the disclosure is to be understood as positioning a prosthesis onto a catheter in a manner so that the catheter is ready to initiate a delivery and deployment procedure to a patient.

A "loading device" according to the disclosure is an assembly of parts comprising e.g. a pulling means, a funnel and a loading tube; it may comprise additional parts or/and functionalities.

The term "locking mechanism" in the sense of the disclosure is to be understood as any means which may connect and keep at least two parts together and allow for release and de-connecting said parts.

The term "useful material" in the sense of the disclosure is to be understood as any materials that are compatible with each other and possibly can be sterilized and/or are low friction materials.

The term "target diameter" in the sense of the disclosure is to be understood as a diameter which allows loading the prosthesis into the tubular structure or/and a diameter which allows the prosthesis to be loaded onto the catheter.

In the following the various aspects of the disclosure will be described in more detail wherein it is to be understood that individual features of the disclosure may be combined in any logical manner beyond the explicit disclosure as mentioned herein below.

In one aspect the problem underlying the application is solved by a pulling means useful for loading a stent or prosthesis onto a delivery system wherein the pulling means has a first diameter, a second diameter and at least three connecting means, preferably mechanical, for linkage (engagement) with a stent or prosthesis.

The pulling means as described above can be engaged with the stent or prosthesis in any manner compatible with the other components of the loading device and/or system as described herein. The engagement of the two parts must fulfill the requirement of an easy connection and disconnection during the loading procedure. The engagement of the different parts must also guarantee that these parts can bear the pulling forces during the loading procedure. One can use e.g., a connecting means which is a releasable connecting means, preferably by way of a latching mechanism, a force-locking mechanism, or a geometrical interlocking.

The pulling means as described herein comprises means which can be engaged with the stent or prosthesis to be loaded onto e.g., a catheter. The pulling means preferably comprises at least three flexible arms, wherein the flexible arms protrude from the first diameter to the second diameter, preferably wherein the pulling means comprises 5 to 19, or 5 to 12, or 7 to 9 flexible arms. The first diameter is essentially the diameter of the self-expandable stent or prosthesis in its expanded state and the second diameter is essentially the one of the stent or prosthesis when compressed or in its crimped state.

The pulling means (102) as described herein exhibits flexible arms for engagement with the stent or prosthesis. The number of flexible arms may vary and it may be designed as it is useful for the functionality of the loading device and system. The stent or prosthesis comprises pulling points for engagement with the pulling means. The pulling means advantageously comprises or exhibits a number of flexible arms corresponding to the number of pulling points of the stent or prosthesis wherein the flexible arms can be connected with the stent or prosthesis.

The pulling means as described herein is characterized by two diameters, wherein the $2^{nd}$ diameter is 7-10 mm (crimped stent outer diameter), preferably 8 to 9 mm, and the $1^{st}$ diameter is 60-80 mm, preferably 50 to 60 mm.

The pulling means and in particular the flexible arms are designed as disclosed hereinabove with the proviso that it does not comprise any suture, thread, filament, yarn or/and fiber.

One advantage of the pulling means according to the disclosure comprising flexible arms is that it exhibits defined force contact and pulling positions which allow for a symmetrical force application and a symmetrical crimping procedure with reduced stress impact on the crimped prosthesis implying less potential damage to its stent and other connected parts like sealing and valve tissue. The flexible arms and their even or/and symmetrical distribution and/or their choice of material, e.g., a metal or plastic, can provide for a pre-defined three-dimensional design. Such a pre-defined three-dimensional design can be aligned with the expanded state of the prosthesis to be loaded. Such a design will result in an optimized co-operation of the prosthesis and the pulling means and thus the loading device and it will result in a smooth loading onto a delivery system with a protecting effect on the fragile material components of the prosthesis like artificial or biological tissue or/and other materials comprised in small dimensions and thus prone to damage. The advantageous design as disclosed herein provides for a linear force during loading in a symmetrical manner and thus to an even force distribution during the loading procedure. The selection of particular connection points of the prosthesis with the flexible arms in addition supports or/and is sufficient for a smooth and material protecting procedure and an even loading procedure. Surprisingly, it is sufficient to connect the prosthesis not on all e.g., eyelets or possible force points and yet the prosthesis maintains essentially its form and/or geometry during the loading procedure.

The pulling means and loading device as disclosed herein have in particular advantages if the prosthesis which is to be loaded has a relative great opening angle of the individual stent cells and thus implies a disadvantageous force transmission during crimping and loading. This is also true for prostheses which are characterized not simply by a cylindrical form but have a differentiated design over the length with varying diameters and wherein the pulling forces are redirected in order to achieve an elongation. Moreover, the pulling means and loading device as disclosed herein advantageously supports an easy and reliable crimping and loading procedure where the prosthesis is characterized by a great diameter to length ratio, and which implies problems for loading the prosthesis correctly onto a delivery system. Such a prosthesis design implies issues with regards to compression of the stent component and difficulties for the loading procedure. For such stent designs the known loading devices and procedures imply problems and only unsatisfying loading and crimping results.

One advantage of the pulling means is that it represents a mechanical link between the stent/prosthesis to be loaded onto a catheter or/and crimped in diameter and the loading device. One other advantage of the disclosure and the solution of the application is that it now is possible to maintain the symmetry or/and uniformity of the stent/prosthesis also during the loading procedure even though the stent/prosthesis does not exhibit high push resistance.

In a further aspect the problem underlying the application is solved by a loading device useful for loading a stent or prosthesis onto a delivery system comprising a pulling means according to claims 1 to 5, a tapered part, e.g., a funnel, and a loading tube, which may also be denoted as an assembly of parts.

A loading device as described above can in addition comprise a pulling means guide (106). The pulling means guide is positioned concentric around the delivery system, just proximal of the stent holder. It exhibits a guidance hole for each of the flexible arms of the pulling means and therefore maintains an equal distance of them to one another. It guides the flexible arms from its wider diameter to the smaller diameter and locks them in place once the final position is achieved.

A loading device as described above will be designed to exhibit an advantageous angle in its inner area. In one aspect the loading device comprises a tapered part characterized in its inner area by an angle of 10-30° over its length, preferably of 15-20° or/and wherein the tapered part over its length in the inner area is designed convex.

The inner diameter of the loading tube will be adapted to the stent or prosthesis which is to be crimped or/and loaded by the system. The inner diameter of the loading tube (104) can be 7 to 10 mm, or 6 to 9 mm.

The assembly of parts (crimping/loading device) thus overcomes the disadvantages of the state of the art at least partially or essentially completely. The braided stent component or the laser cut stent is kept symmetrical and it is now possible that it will be loaded symmetrically to the catheter; accordingly, also damages to the tissue of the valve will essentially be avoided.

In a further aspect the assembly as described above is characterized by further comprising a catheter releasable connected to the stent or stent-based prosthesis.

In another aspect the problem underlying the application is solved by a system comprising a pulling means as described herein and a stent or prosthesis wherein the pulling means and the stent or prosthesis are mechanically connected and wherein said mechanically connected parts are releasable connected.

The system as described above comprises preferably a heart valve replacement system, comprising a stent or prosthesis and a loading device as described above and a delivery system.

A replacement heart valve which can be advantageously loaded is a mitral or tricuspid replacement heart valve. In particular a mitral and tricuspid replacement heart valve designed to exhibit high flexibility in order to adapt to the biological environment of the target implantation site implies difficulties for loading on a delivery system.

This problem is partly related to the ratio of the stent/prosthesis length to outer stent/prosthesis diameter/height. For example, in a tricuspid replacement heart valve prosthesis the outer diameter is typically more than 40 mm and the length of the stent/prosthesis is typically between 20 to 30 mm, e.g. 25 mm. During the loading procedure the dimensions are inversed which implies a challenge for a correct loading device and loading procedure.

These dimensions of state of the art replacement heart valves, e.g., aortic replacement heart valves, in contrast to tricuspid replacement heart valves maintain essentially the same ratio and imply less of a problem as underlying the current application due to the inversion of the dimensions and ratios as is the case for a stent to be loaded in the current stent/prosthesis, e.g., a tricuspid replacement heart valve.

The assembly according to the disclosure herein will not only serve to crimp the stent or stent-based prosthesis but it will be designed in a manner to easily release the catheter with the loaded prosthesis. Accordingly, and where necessary the parts of the assembly will be connectable and detachable in order to facilitate the release procedure of the stent/prosthesis from the catheter. Accordingly, the assembly as described above is releasable connected with a catheter.

The assembly of parts can be made of any useful material known by the skilled person in this field, e.g., polytetrafluorethylene (PTFE), polyoxymethylene (POM). Preferably certain parts exposed to friction use a low friction material or are coated with such a material, e.g., PTFE/Teflon®. In particular the loading tube (104) can be made out of PTFE.

One advantageous aspect of the disclosure pertains to a loading device and system and its corresponding loading procedure that shall be utilized for stents/prostheses which do not exhibit a sufficiently high pushability, stent/prosthesis stiffness to be susceptible to be advanced through a funnel (103).

The solution of the disclosure uses instead the approach that the stent/prosthesis shall be pulled through the funnel to avoid compression and deformation of the stent/prosthesis. This goal and solution are achieved with a specific loading system as described herein.

The main component to achieve this is a pulling means. The pulling means can be a tubular structure with distal elongated members. These distal elongated members are designed to connect to and disconnect from the stent/prosthesis. The pulling means has as many elongated members as connecting points are required to uniformly pull the stents/prosthesis through the funnel.

Other components of the loading device and system as disclosed herein may be a loading tube, possibly with a flared end, and a base to mount all components in place and control their position on the delivery system.

In another aspect the problem underlying the application is further solved by a method for loading a stent or prosthesis onto a delivery system comprising the steps of i. connecting the stent or prosthesis with the pulling means, ii. pulling the stent or prosthesis into and through the tapered part, iii. followed by pulling the stent or prosthesis into the loading tube, iv. engaging the stent or prosthesis with the delivery system, and v. advancing an outer catheter shaft of the delivery system over the stent or prosthesis.

One major advantage of the above described, pulling means, loading system and its corresponding loading method is that the force, which is imposed on the implant during the loading procedure, is distributed evenly over the structure of the implant. This facilitates a uniform crimping behavior, which furthermore is beneficial for the durability of the implant as damages due to high stresses are avoided.

The loading procedure as disclosed herein provides advantageously for a smooth loading with symmetrical movements and crimping of the stent/prosthesis and exhibiting reduced negative impact on the stent and particularly the prosthesis. The elongated members or flexible arms of the pulling means are advanced through a loading tube and a funnel. Its distal ends are connected to the proximal end of the implant. Applying tensile force to the pulling means will pull the stent/prosthesis in an advantageous manner through the funnel and into the loading tube and thereby uniformly reduce it to the crimped diameter. Once the stent/prosthesis is crimped it can be disengaged from the pulling means and be attached to the delivery system, prior to advancing the outer catheter shaft (107) to cover the stent/prosthesis.

The entire procedure can be exerted from the distal or proximal end of the stent/implant.

In one aspect the problem underlying the application is further solved by a method using a pulling means, an assembly of parts, a loading device for crimping a stent or stent-based prosthesis or/and loading a stent or stent-based prosthesis onto a delivery device as described above.

The same advantages as pointed out above for the assembly of parts will apply to the method and achieved by same mutatis mutandis.

In the method as described herein the assembled parts and the catheter may self-align or manually be positioned correctly in each step of the method as useful.

The sequence of the method steps is aligned with the parts of the assembly and the logic of crimping and/or loading the stent or stent-based prosthesis onto the catheter. Accordingly the logic of the method and the method steps depends on the particular part design.

In another aspect the disclosure relates to a system comprising an assembly as described above, a prosthesis and preferably a catheter.

EXAMPLES

The following is a description of preferred aspects of the disclosure, and it shall not be construed to be limiting in any aspect or manner. Moreover, the skilled person will appreciate that any aspect and feature of the disclosure herein above and below can be used and combined with any of the remaining features as disclosed herein. The disclosure shall be understood that any such feature can be combined with any other feature as disclosed herein without being in any sense bound or to be restricted in terms of combination of features.

As can be seen from FIG. 1 according to the disclosure the pulling means [102] is guided over the outer catheter shaft [107]. The elongated members of the pulling means are guided through a loading tube [104] and a funnel [103]. Each of the distal ends of the elongated members is connected to a feature on the stent/prosthesis [101], such as an eyelet or a similar feature. Applying tension to the pulling means towards the proximal side will pull the stent/implant through the funnel into the loading tube. As the loading tube ends just distal of the stent holder [105] (catheter) the stent/prosthesis is pulled so far that the eyelets protrude from the loading tube and sit above the stent holder. The pulling means is disengaged from the stent/prosthesis and the eyelets are engaged with the stent holder. Then the outer catheter shaft is advanced over the prosthesis. The loading tube can be pulled distally to fully crimp the stent/prosthesis and ease the outer catheter shaft advancement.

The sequence of the loading method comprises the steps of connecting the stent/prosthesis with the pulling means, pulling the stent/prosthesis into and through the funnel, disengaging the stent/prosthesis from the pulling means and engaging the stent/prosthesis with the stent holder (delivery system/catheter).

Figure 2:
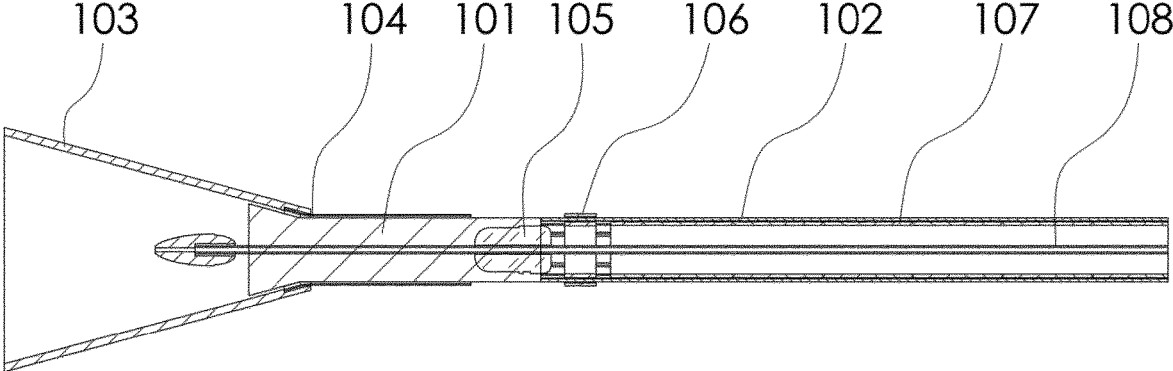
FIG. 2 describes a stent or prosthesis which is partially crimped.

According to the disclosure and as is described in FIG. 2, once the pulling means is pulled out of the loading tube [104] the pulling means guide [106] maintains the diameter of the pulling means. Once the stent/prosthesis [101] is pulled into the loading tube [104] and its eyelets sit above the stent holder [105], they can be engaged with the stent holder. The pulling means is disengaged from the stent/prosthesis, preferably its eyelets, so that the outer catheter shaft [107] can be advanced over the prosthesis.

Figure 3:
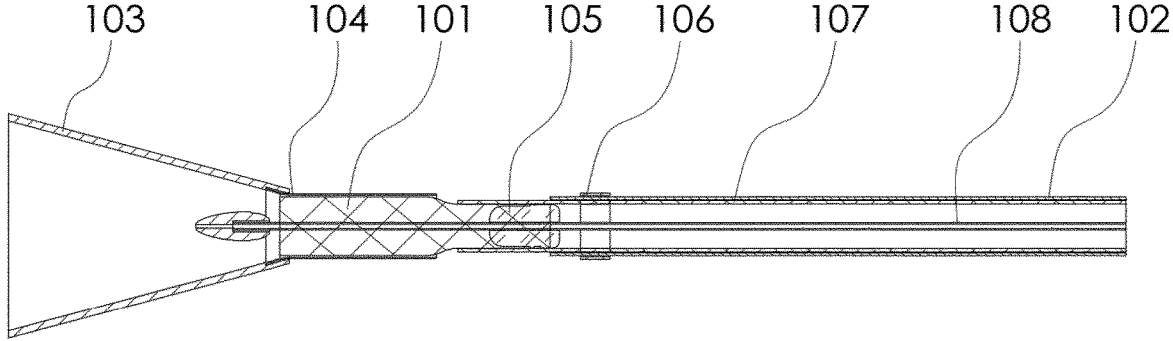
FIG. 3 illustrates a stent or prosthesis which is completely crimped.

In the next step according to the disclosure, and as illustrated in FIG. 3, while outer catheter shaft [107] is advanced over the stent/prosthesis [101] the funnel [103] and loading tube [104] are pulled distally to crimp the distal end of the stent/implant and ease the advancement of the outer catheter shaft [107] over the stent/prosthesis.

The engagement and disengagement of the stent/prosthesis with the pulling means can be achieved by connecting means (e.g., as represented by 109 and 110). Such connecting means have to be characterized in that the two parts may be easily connected and disconnected. A second requirement is that the connecting means must withstand the pulling forces during the loading procedure. Any useful connecting means which fulfills the above requirements can be combined with the other parts of the assembly of parts, loading device and system.

Figure 4:
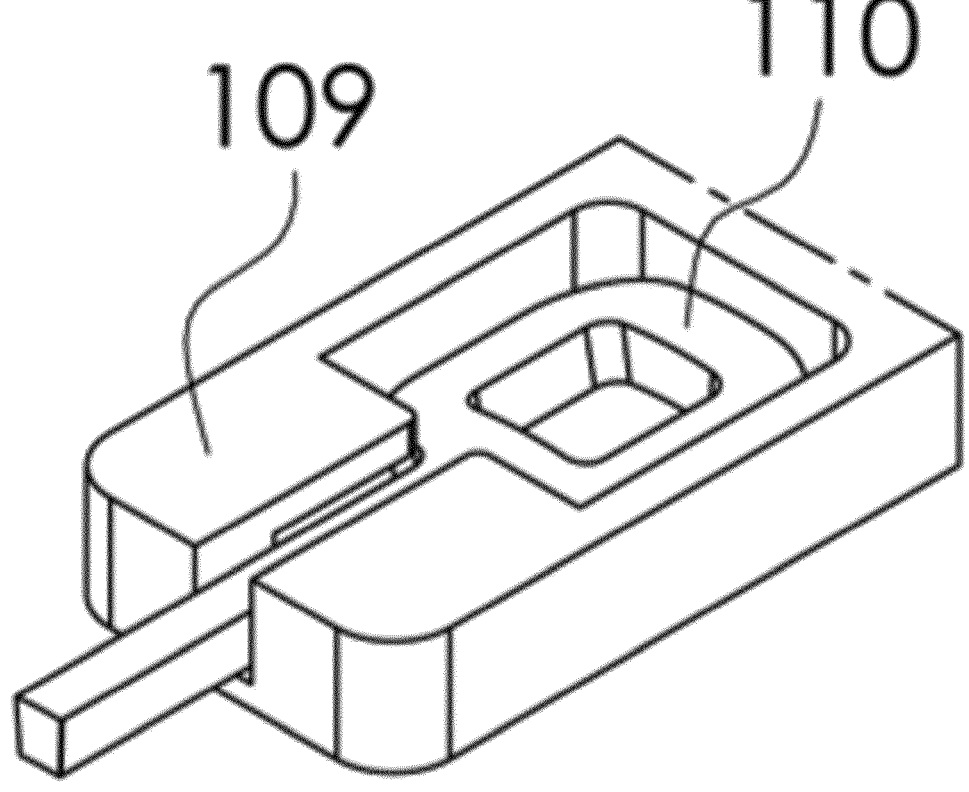
FIG. 4 depicts an eyelet placed into a pocket of a distal end of a pulling means.
Figure 5:
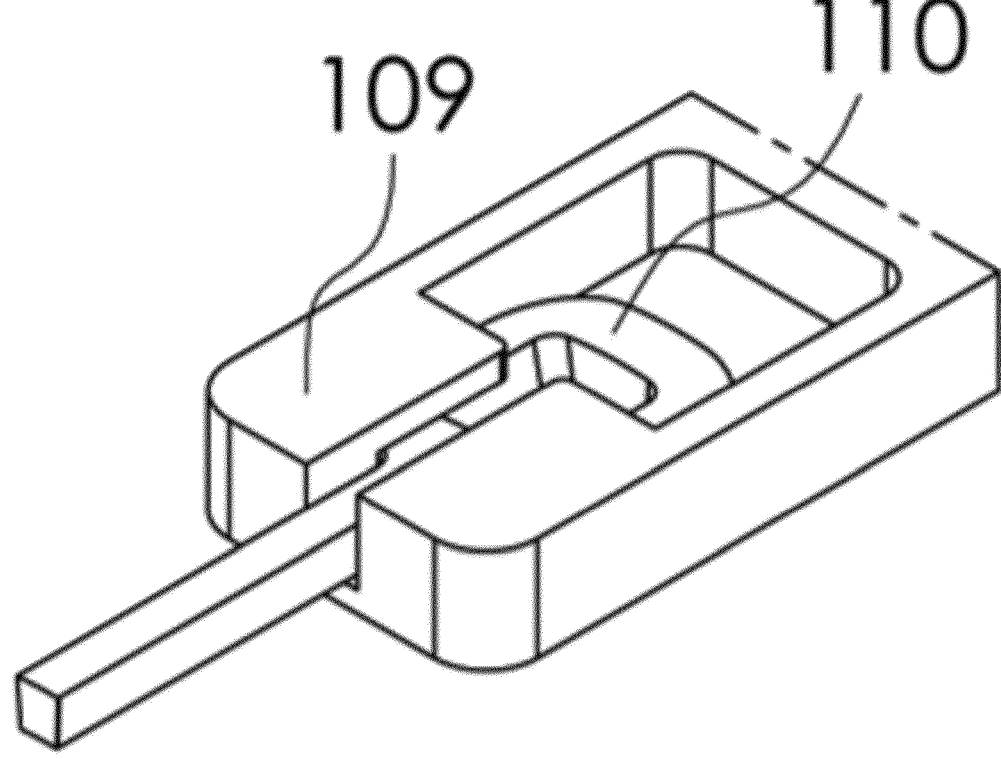
FIG. 5 describes an eyelet engaged with the distal end of a pulling means.

FIG. 4 illustrates an example of a connecting means (connecting means 1) wherein with this connecting means the distal end of the pulling means has a pocket for each eyelet that shall be engaged. The eyelet is placed inside the pocket and then slid downwards (FIG. 5). At the second stage the design and fit between both components and an appropriate tolerancing ensure that the eyelet is securely attached but can also be disconnected by applying push-pressure to the pulling means, which moves the eyelet back up into the pocket.

Figure 6:
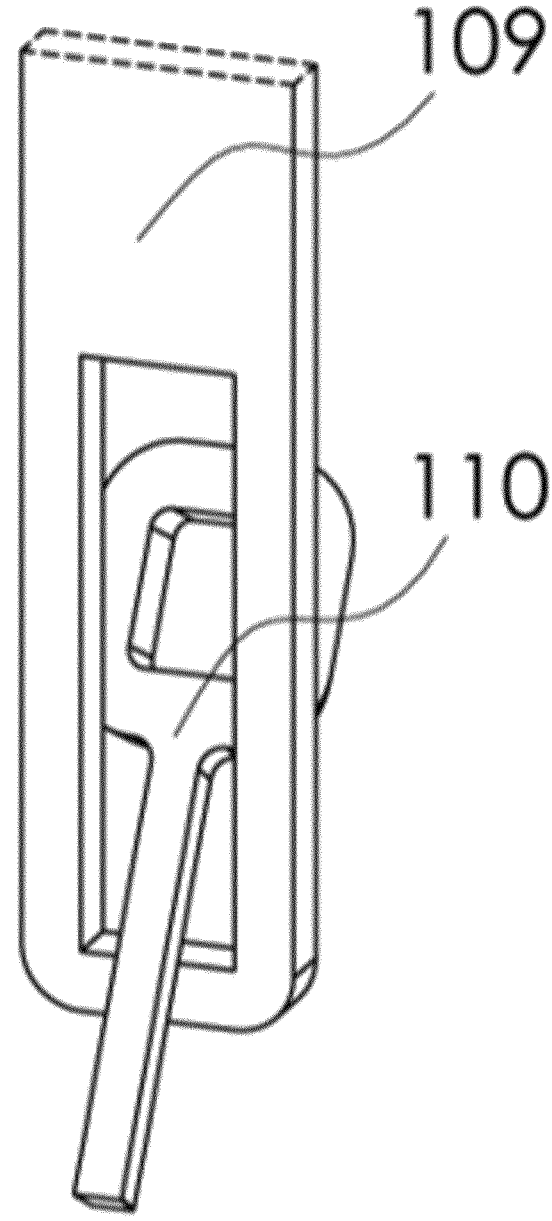
FIG. 6 shows a stent or prosthesis eyelet engaged in an eyelet at a distal end of a pulling means.
Figure 7:
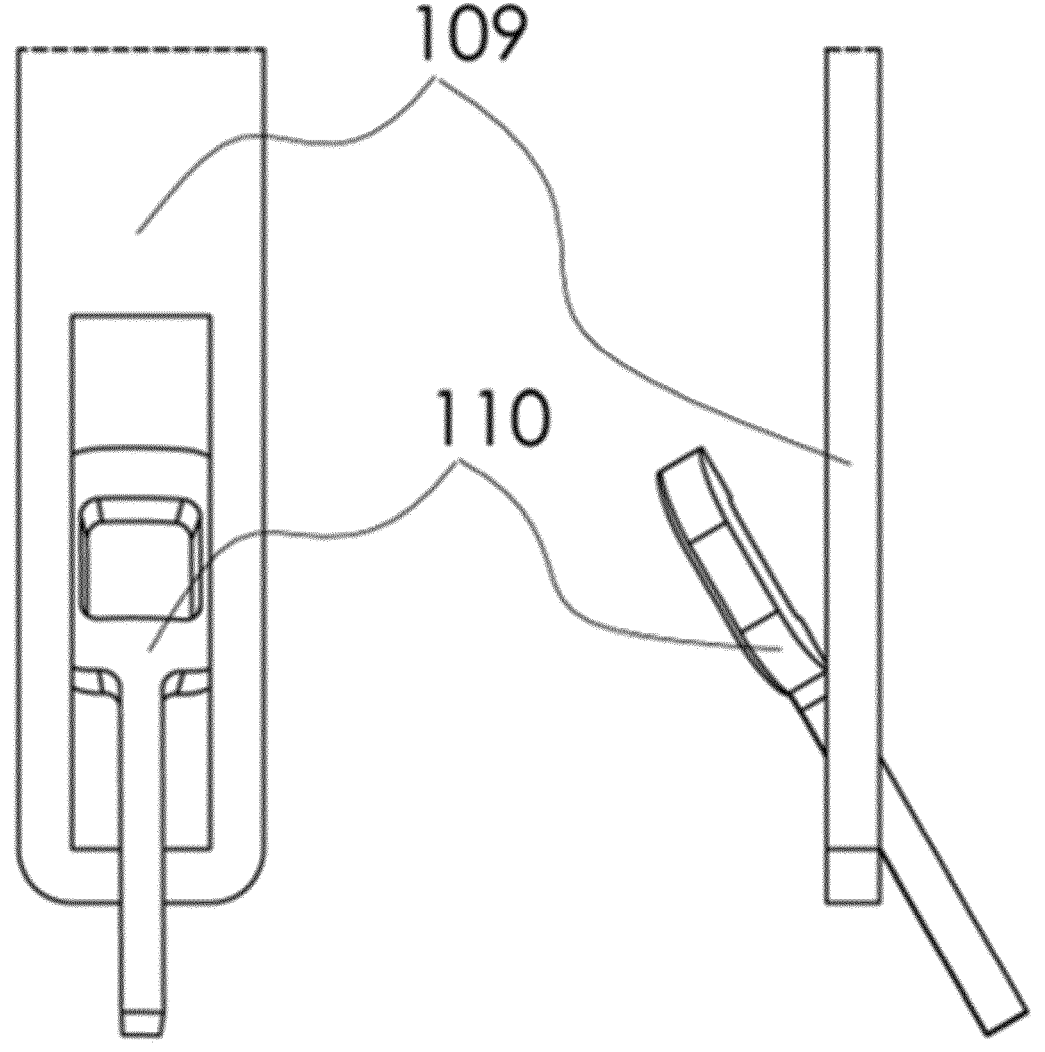
FIG. 7 depicts a view of FIG. 6 turned 90° wherein the stent or prosthesis eyelet is engaged in an eyelet at a distal end of a pulling means.
Figure 8:
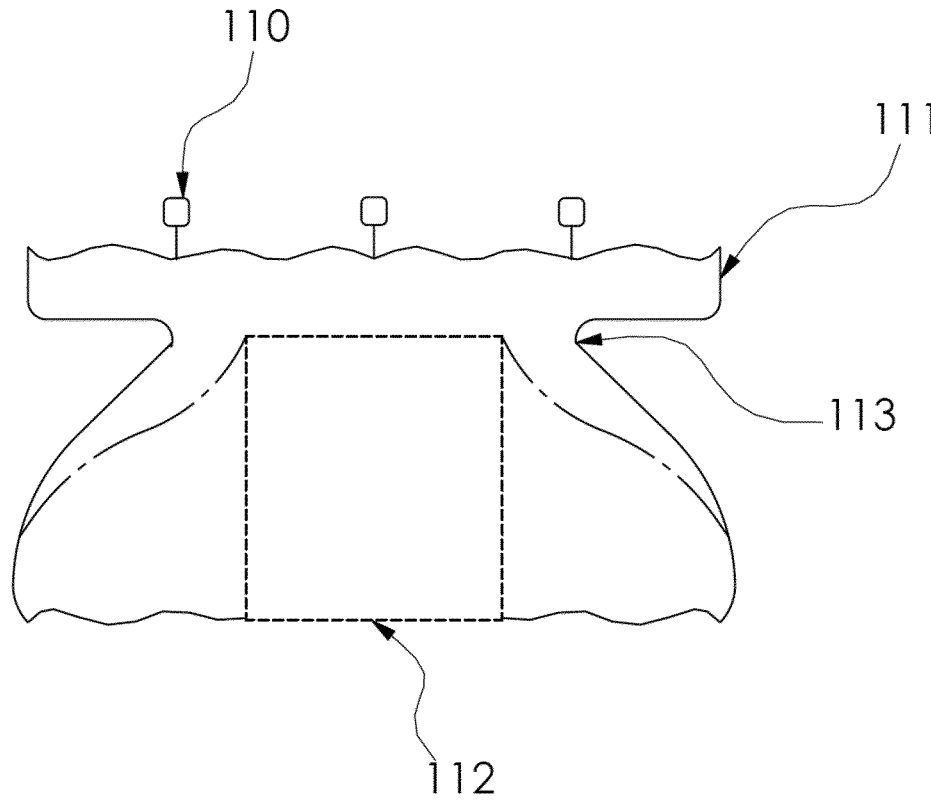
FIG. 8 illustrate one aspect of the disclosure which is a stent/prosthesis which can be loaded with the loading device as disclosed herein, i.e., a double stent prosthesis, wherein distally the outer stent (111) is connected through connecting arms with the inner stent (112). The design feature of the V-groove (113) is one reason why common loading and crimping techniques cannot be applied to this design.
Figure 9:
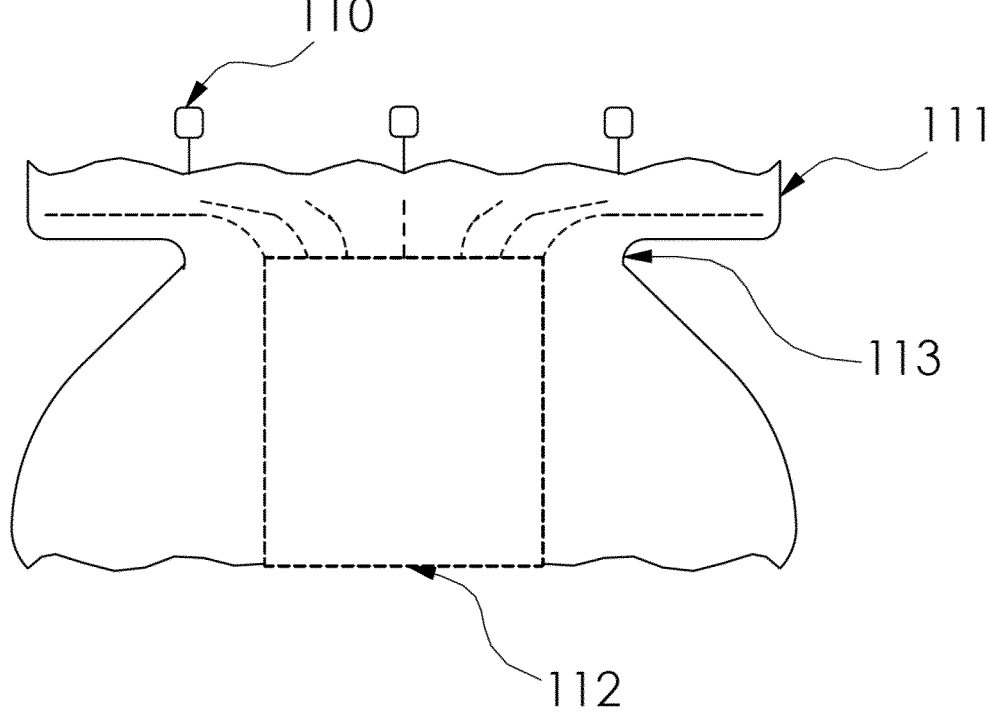
FIG. 9 illustrates one aspect of the disclosure which is a stent/prosthesis which can be loaded with the loading device as disclosed herein. Compared to FIG. 8 this schematic illustrates a different connection mechanism between the inner stent (112) and the outer stent (111). This example can be a two or three part stent design.
Figure 10:
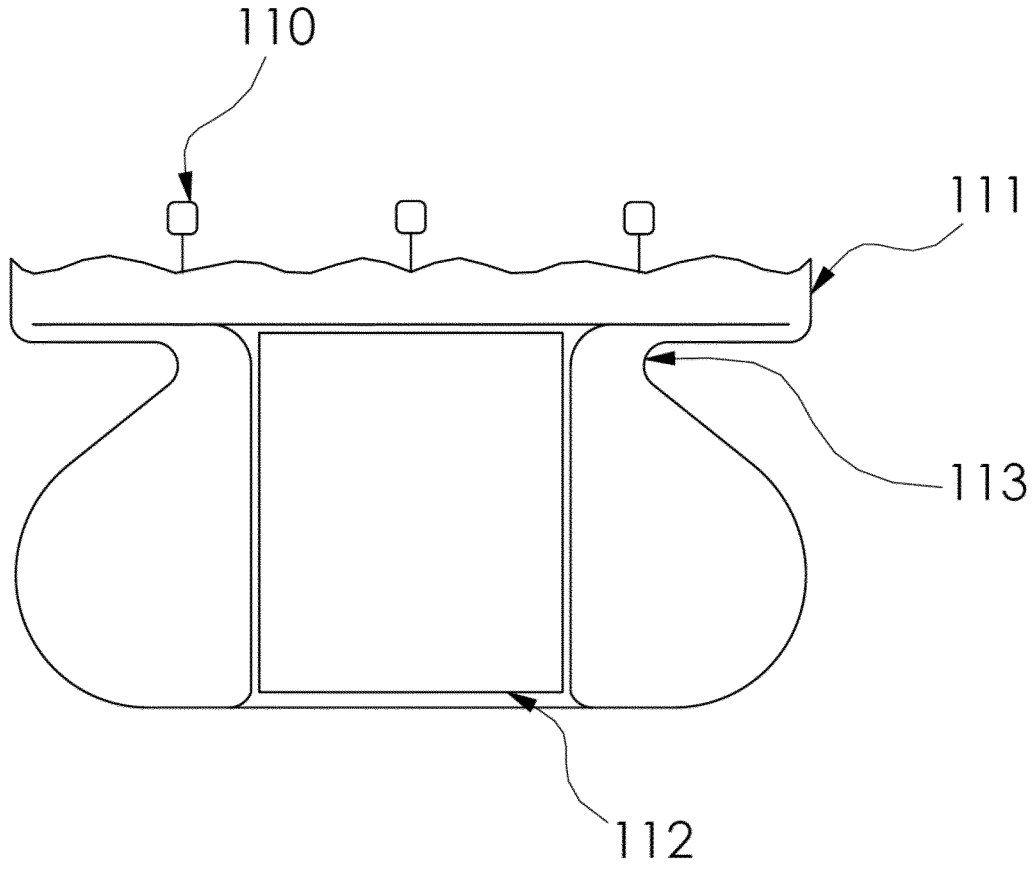
FIG. 10 illustrates one aspect of the disclosure which is a stent/prosthesis which can be loaded with the loading device as disclosed herein. This is an example of a dual stent with a braided outer stent and a laser-cut inner stent.
Figure 11:
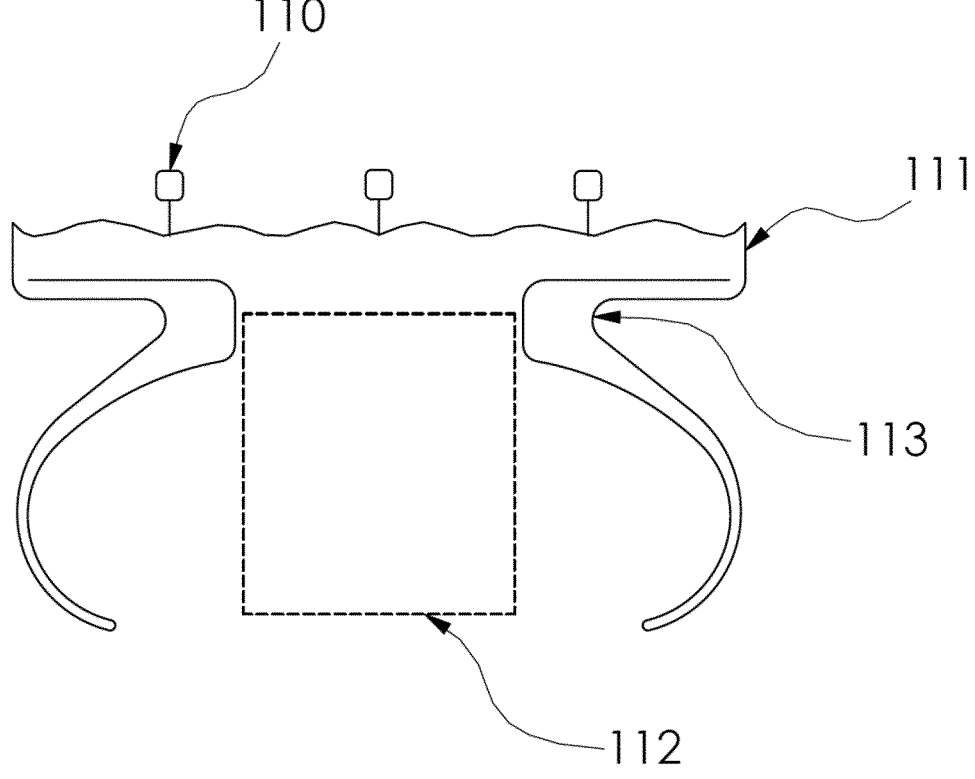
FIG. 11 illustrates one aspect of the disclosure, wherein the prosthesis is depicted in a cut representation. The inner stent (112) and braided mesh outer stent (111) is shown as well as a V or U groove (113).

Examples of connecting means are also illustrated in FIGS. 5, 6 and 7 (connecting means 2), wherein with this connecting means the distal end of the pulling means exhibits a rectangular eyelet. The eyelet of the stent/prosthesis is engaged with the eyelet of the pulling means. To engage and disengage both parts the distal ends of the pulling means need to be turned to slide them sideways over the stent/prosthesis eyelet.

FIGS. 8 to 11 illustrate various examples of stents or/and prostheses or/and replacement heart valve prostheses which can be loaded in an advantageous manner onto a delivery system by use of the loading device as described herein and for use in minimally invasive delivery or catheter based delivery of the medical devices illustrated and disclosed herein.

The disclosure thus also encompasses a system comprising a delivery system, a pulling means or/and loading device and a medical device, e.g., a stent, a prosthesis or/and a replacement heart valve prosthesis as described herein.

REFERENCE NUMBER LIST

101 Prosthesis
102 Pulling means
103 Funnel
104 Loading tube
105 Stent holder
106 Pulling means guide
107 Outer catheter shaft
108 Inner catheter shaft
109 Pocket at distal end of pulling means
110 Eyelet of stent or prosthesis
111 Outer stent
112 Inner stent
113 V or U groove

What is claimed is:

1. A loading device useful for loading a tricuspid stent or prosthesis onto a delivery system comprising:
   a tapered part;
   a loading tube;
   a stent holder proximal from the tapered part;
   a pulling means;
   a catheter configured for advancing over the tricuspid stent or prosthesis when in a crimped state; and
   a pulling means guide proximal from the stent holder and over a portion of the catheter;
   wherein the pulling means is configured for pulling the tricuspid stent or prosthesis through the tapered part and into the loading tube, wherein the pulling means has a first diameter, a second diameter and at least three releasable connecting parts for linkage with the tricuspid stent or prosthesis, wherein each of the three releasable connecting parts includes i) an eyelet or ii) a pocket or aperture, and the pulling means exhibit reduced push resistance and allow for a symmetric force application;

wherein the pulling means guide has a guidance hole for each of the pulling means and maintains the pulling means at an equal distance to one another at the second diameter.

2. The loading device according to claim 1, wherein the tapered part is characterized in its inner area by an angle of 10° to 30° over its length or/and wherein the tapered part over its length in the inner area is designed convex.

3. The loading device according to claim 1 wherein an inner diameter of the loading tube is 7 to 10 mm.

4. A system comprising:
   a loading device comprising:
      a tapered part;
      a loading tube;
      a stent holder proximal from the tapered part;
      a pulling means;
      a catheter configured for advancing over a stent or prosthesis when in a crimped state; and
      a pulling means guide proximal from the stent holder and over a portion of the catheter;
      wherein the pulling means is configured for pulling the stent or prosthesis through the tapered part and into the loading tube,
      wherein the pulling means has a first diameter, a second diameter and at least three releasable connecting parts for linkage with the stent or prosthesis, wherein each of the three releasable connecting parts includes i) an eyelet or ii) a pocket or aperture, and the pulling means exhibit reduced push resistance and allow for a symmetric force application;
      wherein the pulling means guide has a guidance hole for each of the pulling means and maintains the pulling means at an equal distance to one another at the second diameter;
   a stent or prosthesis;
   wherein the pulling means and the stent or prosthesis are mechanically connected.

5. A system, comprising:
   a stent or prosthesis;
   a delivery system including:
      a catheter configured for advancing over the stent or prothesis when in a crimped state; and
   a loading device comprising:
      a tapered part;
      a loading tube;
      a stent holder proximal from the tapered part;
      a pulling means; and
      a pulling means guide proximal from the stent holder and over a portion of the catheter;
      wherein the pulling means is configured for pulling the stent or prosthesis through the tapered part and into the loading tube,
      wherein the pulling means has a first diameter, a second diameter and at least three releasable connecting parts for linkage with the stent or prosthesis, wherein each of the three releasable connecting parts includes i) an eyelet or ii) a pocket or aperture, and the pulling means exhibit reduced push resistance and allow for a symmetric force application;

wherein the pulling means guide has a guidance hole for each of the pulling means and maintains the pulling means at an equal distance to one another at the second diameter.

6. The loading device of claim 1, wherein the tapered part is a funnel;

the tapered part is characterized in its inner area by an angle of 15-20° over its length or/and wherein the tapered part over its length in the inner area is convex; and an inner diameter of the loading tube is 7 to 10 mm.

7. The loading device according to claim 1, wherein the pulling means comprises at least three flexible arms, wherein the flexible arms protrude from the first diameter to the second diameter, wherein the stent holder is configured to hold the tricuspid stent or prothesis in a crimped state.

8. The loading device according to claim 7, wherein the tricuspid stent or prosthesis has at least three pulling points, wherein each of the at least three flexible arms corresponds to one of the pulling points of the tricuspid stent or prosthesis wherein each of the flexible arms is connected with the corresponding pulling point of the tricuspid stent or prosthesis during loading of the tricuspid stent or prosthesis into the stent holder.

9. The loading device according to claim 7, wherein the first diameter is 7-10 mm and the second diameter is 60-80 mm.

10. The loading device of claim 1, wherein the at least three releasable connecting parts are mechanical connecting means for linkage with the triscupid stent or prosthesis.

11. The loading device of claim 10, wherein the pulling means comprises 5 to 12 flexible arms, the first diameter is 8 to 9 mm, and the second diameter is 50 to 60 mm.

12. The loading device of claim 6, wherein the tapered part is a funnel;

the tapered part is characterized in its inner area by an angle of 10 to 30° over its length or/and wherein the tapered part over its length in the inner area is convex; and an inner diameter of the loading tube is 7 to 10 mm.

13. The loading device of claim 12, wherein the pulling means comprises 5 to 19 flexible arms that protrude from a first diameter of 7 to 10 mm to a second diameter of 60 to 80 mm, each of the flexible arms corresponds to a pulling points of the tricuspid stent or prosthesis to be connected.

14. The loading device of claim 1, wherein the stent holder comprises releasable connecting parts, so that the tricuspid stent or prosthesis may be disengaged from the pulling means and engaged with the stent holder.

15. The loading device of claim 1, wherein the pulling means is between an outer wall of an inner catheter shaft and an inner tapered wall of the tapered part.

16. The loading device of claim 1, wherein the pulling means is positioned between an inner wall of the loading tube and the stent holder, and wherein a proximal end of the loading tube is at a proximal end of the tapered part.

17. The loading device of claim 1, wherein the releasable connecting parts are eyelets on the pulling means corresponding to pockets on the stent or prosthesis, or the releasable connecting parts are pockets on the pulling means and the stent or prosthesis includes counterpart eyelets;

wherein the eyelet in one orientation can enter into an opening of the pocket and/or the eyelet slides into the pocket.

\* \* \* \* \*